US010278569B2

(12) United States Patent
Amano

(10) Patent No.: US 10,278,569 B2
(45) Date of Patent: May 7, 2019

(54) MEDICAL CAMERA HEAD AND MEDICAL CAMERA APPARATUS INCLUDING A HEAT TRANSFER MEMBER

(71) Applicant: SONY OLYMPUS MEDICAL SOLUTIONS INC., Tokyo (JP)

(72) Inventor: Kohtaro Amano, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 196 days.

(21) Appl. No.: 15/092,796

(22) Filed: Apr. 7, 2016

(65) Prior Publication Data

US 2016/0338580 A1     Nov. 24, 2016

(30) Foreign Application Priority Data

May 22, 2015   (JP) ................................ 2015-104597

(51) Int. Cl.
| | | |
|---|---|---|
| *H04N 5/225* | (2006.01) | |
| *A61B 1/00* | (2006.01) | |
| *A61B 1/05* | (2006.01) | |
| *A61B 1/005* | (2006.01) | |
| *A61B 1/045* | (2006.01) | |
| *A61B 1/07* | (2006.01) | |

(52) U.S. Cl.
CPC .......... *A61B 1/051* (2013.01); *A61B 1/00114* (2013.01); *A61B 1/053* (2013.01); *H04N 5/2252* (2013.01); *H04N 5/2256* (2013.01); *A61B 1/005* (2013.01); *A61B 1/00006* (2013.01); *A61B 1/00009* (2013.01); *A61B 1/00045* (2013.01); *A61B 1/045* (2013.01); *A61B 1/07* (2013.01); *H04N 2005/2255* (2013.01)

(58) Field of Classification Search
None
See application file for complete search history.

(56) References Cited

U.S. PATENT DOCUMENTS 4,701,829 A  * 10/1987 Bricaud ............. H05K 7/20636
165/185
2003/0222227 A1 * 12/2003 Richards ............... H01J 37/244
250/492.21
(Continued)

FOREIGN PATENT DOCUMENTS

| JP | 2007-143821 | 6/2007 |
|---|---|---|
| JP | 2012-195931 | 10/2012 |

(Continued)

OTHER PUBLICATIONS

Office Action dated Feb. 12, 2019, in Japanese Patent Application No. 2015-104597 (with English-language translation), 9 pgs.

*Primary Examiner* — Edemio Navas, Jr.
(74) *Attorney, Agent, or Firm* — Oblon, McClelland, Maier & Neustadt. L.L.P.

(57) ABSTRACT

There is provided a medical camera head including: a first casing configured to accommodate an imaging element; a heat-generating section accommodated in the first casing; a connection section provided in the first casing, an external signal transmission section being connected to one end of the connection section; and a heat transfer member interposed between the heat-generating section and the other end of the connection section.

8 Claims, 4 Drawing Sheets

(56) References Cited

U.S. PATENT DOCUMENTS

| | | | |
|---|---|---|---|
| 2007/0158574 A1* | 7/2007 | Petrillo | G01T 1/2018 250/370.13 |
| 2013/0085326 A1* | 4/2013 | Scheller | A61M 3/0266 600/106 |
| 2014/0206939 A1* | 7/2014 | Eisele | A61B 1/128 600/156 |
| 2014/0333743 A1* | 11/2014 | Gilreath | A61B 1/00009 348/74 |

FOREIGN PATENT DOCUMENTS

| JP | 2014-133046 | 7/2014 |
|---|---|---|
| WO | WO 2015/045456 A1 | 4/2015 |

\* cited by examiner

MEDICAL CAMERA HEAD AND MEDICAL CAMERA APPARATUS INCLUDING A HEAT TRANSFER MEMBER

CROSS REFERENCE TO RELATED APPLICATIONS

This application claims the benefit of Japanese Priority Patent Application JP 2015-104597 filed May 22, 2015, the entire contents of which are incorporated herein by reference.

BACKGROUND

The present disclosure relates to medical camera heads and medical camera apparatuses.

In the medical field, camera apparatuses such as endoscope apparatuses have been used to observe an observation target in related art. Used in such a camera apparatus is a medical camera head (hereinafter also simply called a camera head) that images an observation target by an internal imaging element, such as an endoscope camera head connected to a rigid endoscope. The camera head outputs an image signal obtained by the imaging to other equipment. Then, an image of the observation target obtained by the camera apparatus is recorded, or displayed on a display apparatus to be observed by a plurality of persons during surgery. The camera head is used with a user grasping it for the purpose of moving the camera head in order to move its position in the observation target, or pressing a switch provided on the camera head in order to perform various operations of the camera head. To improve the operability of such a camera head, for example, there have been proposed technologies for reducing a camera head in size.

For example, JP 2012-195931A discloses a technology of improving the heat dissipation efficiency of a heat-generating member inside a medical camera head.

SUMMARY

Unfortunately, the existing technologies related to observation apparatuses in the medical field find it difficult to acquire high-quality images with small size and weight in some cases. For example, acquiring high-definition images of the observation target increases the amount of image data to be processed by the medical camera head, resulting in an increase in the amount of heat generated by processing the image data. In such a case, in the technology disclosed in JP 2012-195931A, heat generated inside the medical camera head is transferred to a casing to be dissipated; however, in order to dissipate the increased amount of generated heat, an outer surface of the casing is made larger, which makes the medical camera head larger and heavier and unsuitable for grasping by the user in some cases. In addition, since the casing can be grasped by the user, heat dissipation efficiency from the casing to the outside air decreases, increasing the temperature of the imaging element inside the casing and making it difficult to acquire high-quality images, in some cases.

Hence, an embodiment of the present disclosure proposes a novel and improved medical camera head and medical camera apparatus that are capable of acquiring high-quality images with small size and weight.

According to an embodiment of the present disclosure, there is provided a medical camera head including: a first casing configured to accommodate an imaging element; a heat-generating section accommodated in the first casing; a connection section provided in the first casing, an external signal transmission section being connected to one end of the connection section; and a heat transfer member interposed between the heat-generating section and the other end of the connection section.

According to an embodiment of the present disclosure, there is provided a medical camera apparatus including: the medical camera head; and the signal transmission section connected to the connection section of the medical camera head.

According to an embodiment of the present disclosure, there is provided a medical camera apparatus including: a medical camera head including a first casing that is configured to accommodate an imaging element and at least partly includes a metal portion, a heat-generating section accommodated in the first casing, and a heat transfer member interposed between the heat-generating section and the metal portion; and a signal transmission section that includes a second casing and is connected to the medical camera head, the second casing being in contact with the metal portion of the first casing and made of a resin containing an electrically conductive filler.

According to an embodiment of the present disclosure, high-quality images can be acquired with small size and weight.

Note that the effects described above are not necessarily limited, and along with or instead of the effects, any effect that is desired to be introduced in the present specification or other effects that can be expected from the present specification may be exhibited.

DETAILED DESCRIPTION OF THE EMBODIMENT(S)

Figure 1:
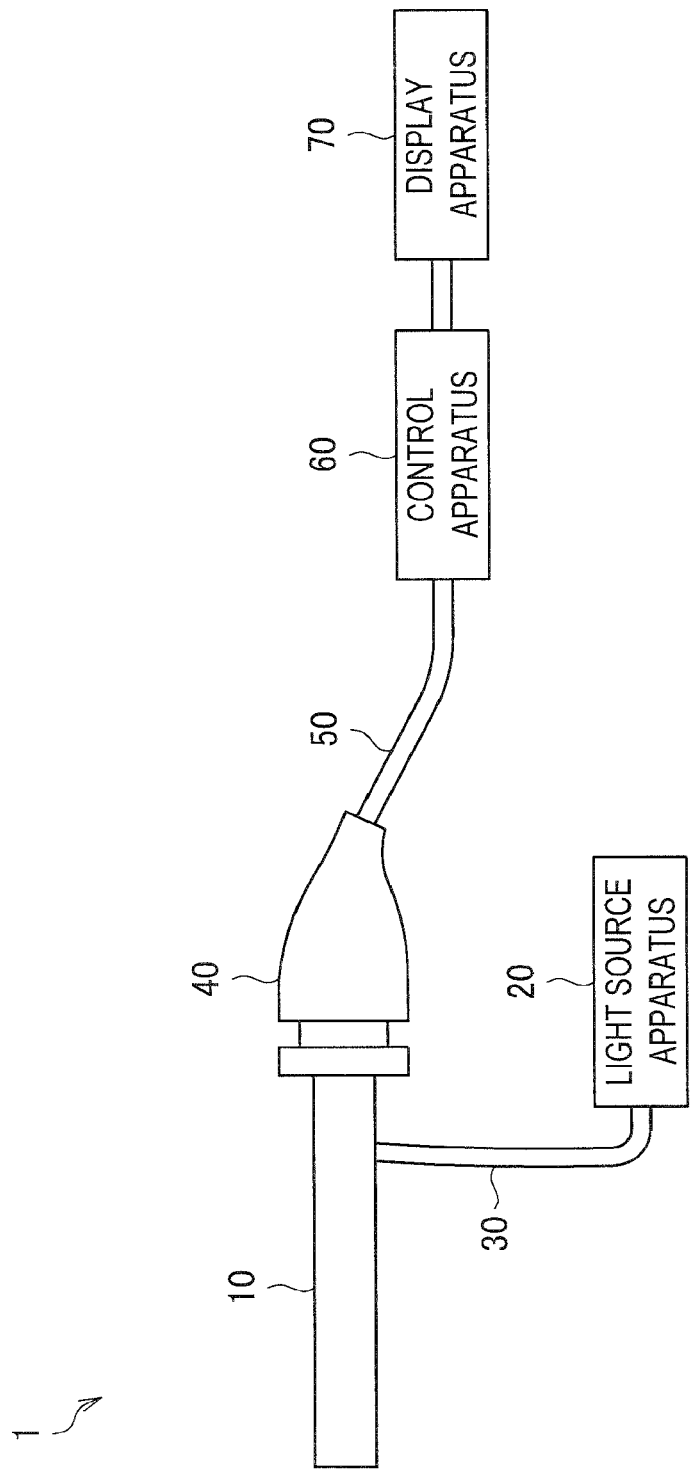
FIG. 1 is an explanatory diagram illustrating a schematic configuration of an example of an endoscope apparatus according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Description is given in the following order.

1. Endoscope apparatus according to embodiment of the present disclosure
2. Camera head according to embodiment of the present disclosure
   2-1. Schematic configuration of camera head 2-2. Connection of heat transfer member to signal processing section and hermetic connector
3. Effects
4. Conclusion

1. Endoscope Apparatus According to Embodiment of the Present Disclosure

First, a schematic configuration of an endoscope apparatus 1 according to an embodiment of the present disclosure will be described referring to FIG. 1.

FIG. 1 is an explanatory diagram illustrating a schematic configuration of an example of the endoscope apparatus 1 according to an embodiment of the present disclosure. The endoscope apparatus 1 is an example of a medical camera apparatus according to an embodiment of the present disclosure. The endoscope apparatus 1 includes, as illustrated in FIG. 1, an insertion section 10, a light source apparatus 20, a light guide 30, a camera head 40, a cable 50, a control apparatus 60, and a display apparatus 70.

The insertion section 10 is slender and includes therein an optical system that concentrates incident light. The front end of the insertion section 10 is inserted into a patient's body cavity, for example. The rear end of the insertion section 10 is detachably connected to the front end of the camera head 40. In addition, the insertion section 10 is connected to the light source apparatus 20 via the light guide 30, and receives light supplied from the light source apparatus 20.

The light source apparatus 20 is connected to the insertion section 10 via the light guide 30. The light source apparatus 20 supplies light to the insertion section 10 via the light guide 30. The light supplied to the insertion section 10 is emitted from the front end of the insertion section 10 to illuminate an observation target, such as a tissue inside a patient's body cavity. Reflected light from the observation target is concentrated by the optical system inside the insertion section 10.

The camera head 40 has a function of imaging the observation target. The camera head 40 is connected to the control apparatus 60 via the cable 50, which is a signal transmission section. The camera head 40 images the observation target by photoelectrically converting the reflected light from the observation target concentrated by the insertion section 10, and outputs an image signal obtained by the imaging to the control apparatus 60 via the cable 50. Note that details of the camera head 40 will be described later.

The control apparatus 60 controls the camera head 40, and also performs predetermined processing on the image signal output from the camera head 40 and then outputs the image signal to the display apparatus 70. Note that the control apparatus 60 may store an image of the observation target based on the image signal.

The display apparatus 70 displays an image of the observation target on the basis of the image signal output from the control apparatus 60. This function is implemented by, for example, a cathode ray tube (CRT) display apparatus, a liquid crystal display (LCD) apparatus, or an organic EL display (organic light emitting diode) apparatus. The image of the observation target displayed by the display apparatus 70 is observed by a plurality of persons during surgery, for example.

2. Camera Head According to Embodiment of the Present Disclosure

2-1. Schematic Configuration of Camera Head

Next, a schematic configuration of the camera head 40 according to an embodiment of the present disclosure will be described referring to FIG. 2.

Figure 2:
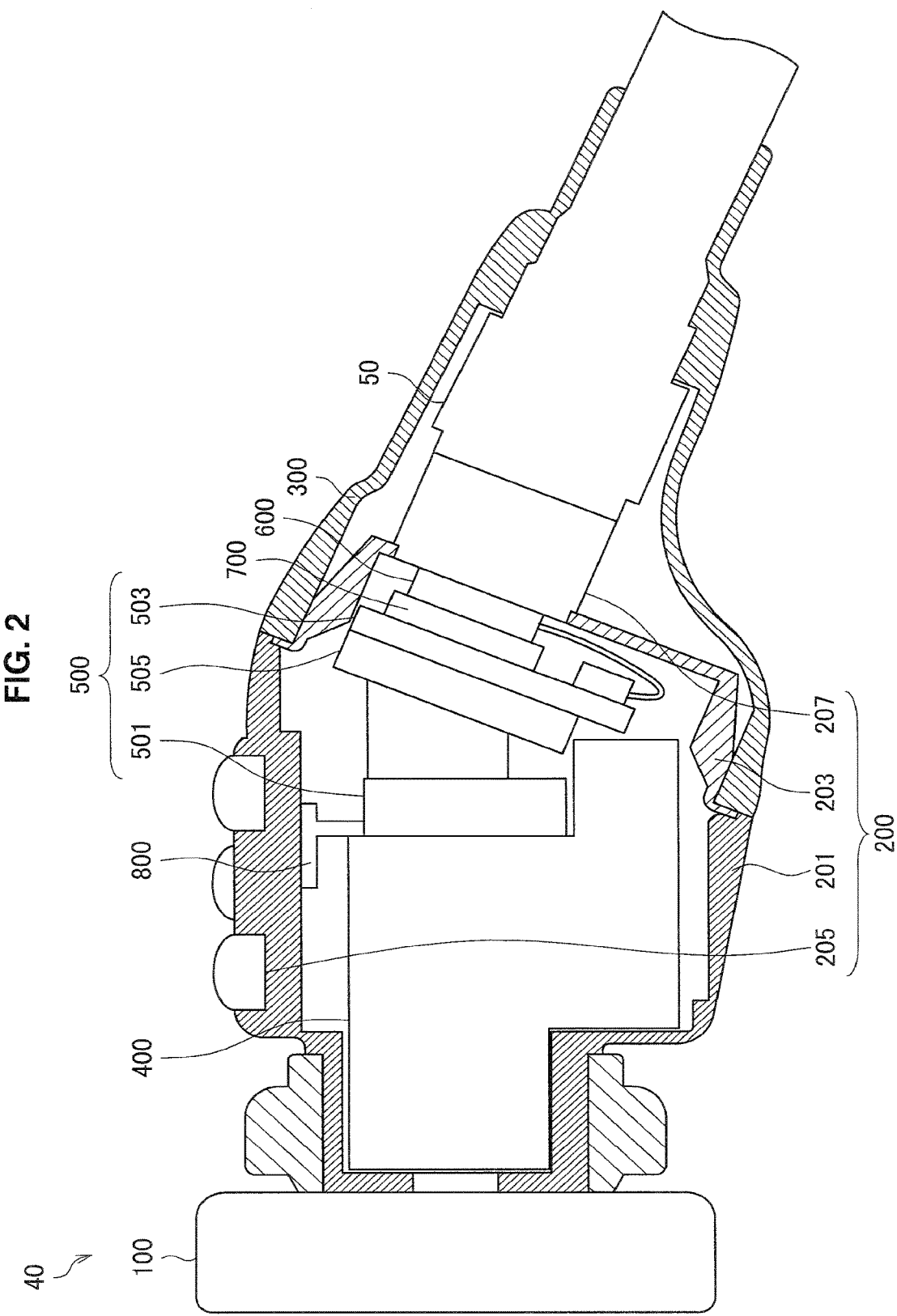
FIG. 2 is a cross-sectional view of a schematic configuration of an example of a camera head according to an embodiment of the present disclosure.

FIG. 2 is a cross-sectional view of a schematic configuration of an example of the camera head 40 according to an embodiment of the present disclosure. As illustrated in FIG. 2, the camera head 40 includes a coupler section 100, a first casing section 200, a lens unit 400, a main board 500, which is an imaging board, a connector connection board 600, a heat transfer member 700, and a switch connection board 800.

The coupler section 100 is provided at the front end of the camera head 40 and detachably connected to the insertion section 10. At the rear end of the coupler section 100 is provided the first casing section 200.

The first casing section 200 includes a front casing 201, a rear casing 203, a switch 205 provided on an outer circumferential surface of the front casing 201, and a hermetic connector 207 provided at the rear end of the rear casing 203. The first casing section 200 air-tightly accommodates the lens unit 400, the main board 500, the connector connection board 600, the heat transfer member 700, and the switch connection board 800. This prevents intrusion of foreign substances, such as moisture, into the first casing section 200 from the outside.

The front casing 201 and the rear casing 203 are metal casings of titanium, a titanium alloy, or SUS, for example, each having a substantially cylindrical shape, and are connected by welding, for example. To the front casing 201 of the camera head 40 is connected, from the rear casing 203 side, a second casing section 300, which is part of the cable 50, and an outer surface of the rear casing 203 is covered by the second casing section 300. These front casing 201 and rear casing 203 cover the lens unit 400, the main board 500, the connector connection board 600, the heat transfer member 700, and the switch connection board 800. The front casing 201, the rear casing 203, and the hermetic connector 207 of the first casing section 200 can partly or wholly constitute a metal portion of the first casing section 200.

The switch 205 is provided on the outer circumferential surface of the front casing 201 and connected to an imaging element mounting section 501 via the switch connection board 800. One or more switches 205 are provided, for example, and a user can perform various operations by pushing the switches 205.

The hermetic connector 207 is an example of a connection section according to an embodiment of the present disclosure. The hermetic connector 207 penetrates the rear end of the rear casing 203 and is connected to the rear casing 203 by welding, for example. The front end portion of the hermetic connector 207 is placed inside the first casing section 200, and the rear end portion of the hermetic connector 207 is placed outside the first casing section 200. The cable 50 outside the first casing section 200 is connected to the rear end portion of the hermetic connector 207. Specifically, the hermetic connector 207 is a connector section having the rear end portion to which the cable 50 outside the first casing section 200 is detachably connected. Note that details of the hermetic connector 207 will be described later.

The second casing section 300, which is part of the cable 50, is in contact with the first casing section 200 of the camera head 40 and covers the hermetic connector 207, which is a connection section between the camera head 40 and the cable 50. Specifically, the second casing section 300 is placed behind the front casing 201 and connected to a rear end surface of the front casing 201. This allows the second casing section 300 to cover part of the rear casing 203, the hermetic connector 207, and part of the cable 50. That is, the front casing 201 of the first casing section 200 and the second casing section 300 constitute an outer surface of the camera head 40, and this portion is grasped when the user uses the camera head 40. For example, when the user uses the camera head 40, the first casing section 200 can be at least partly grasped. Specifically, the front casing 201 of the first casing section 200 can be grasped. The second casing section 300 may cover the signal processing section 503.

The second casing section 300 is preferably a material having an excellent heat dissipation property and having electrical conductivity in order to suppress static electricity, and for example, may be made of a resin containing a metal or an electrically conductive filler.

For example, an electrically conductive filler included in the second casing section 300 may contain a carbon allotrope. Specifically, as the electrically conductive filler included in the second casing section 300, graphite, a carbon fiber, a carbon nanotube, or the like can be used. To suppress a local temperature rise in the second casing section 300, a resin containing an electrically conductive filler generally having thermal conductivity is used.

As a resin constituting the second casing section 300, in the case of making the camera head adaptable to an autoclave, a resin having resistance to high-temperature high-pressure water vapor in autoclave sterilization is specifically used. More specifically, as the resin constituting the second casing section 300, an ABS resin, nylon, polypropylene (PP), polymethyl methacrylate (PMMA), polyurethane (PU), polycarbonate (PC), polybutylene terephthalate (PBT), a polyamide (PA), polyphenylene oxide (PPO) (registered trademark), syndiotactic polystyrene (SPS) (registered trademark), polyethersulfone (PES), polyphenylene sulfide (PPS), polyetherimide (PEI), a liquid crystal polymer (LCP), PC/ABS, PC/acrylonitrile-styrene-acrylate (ASA), PEEK, or the like can be used. With consideration given also to chemical resistance for sterilization and disinfection, particularly preferable examples of the resin constituting the second casing section 300 include polyetheretherketone (PEEK), polyetherimide (PEI), polyphenylsulfone (PPSU), polyphenylene sulfide (PPS), polyarylate (PAR), and polysulfone (PSF). The front casing 201 made of a metal and the rear casing 203 made of an electrically conductive resin form the outer surface of the camera head 40.

The lens unit 400 is provided at the front end of the first casing section 200. At the rear end of the lens unit 400 is placed the imaging element mounting section 501 where an imaging element, such as a complementary metal oxide semiconductor (CMOS) image sensor or a charge coupled device (CCD) image sensor, is mounted. The lens unit 400 concentrates the reflected light from the observation target that is emitted from the insertion section 10 connected to the coupler section 100, thereby forming an image of the observation target on an imaging surface of the imaging element.

The main board 500 includes three rigid portions: the imaging element mounting section 501 where the imaging element is mounted, a signal processing section 503 where a signal processing circuit is mounted, and an electronic component mounting section 505 where an electronic component, such as a power supply circuit, is mounted. The signal processing section 503 is electrically connected to the imaging element mounting section 501 by a flexible portion, and the signal processing section 503 is electrically connected to the electronic component mounting section 505 by a flexible portion. The main board 500 is accommodated in the first casing section 200 in a state where the flexible portions are bent.

The imaging element mounting section 501 photoelectrically converts, by the imaging element, the reflected light from the observation target concentrated by the lens unit 400, thereby acquiring an image signal representing the observation target. Then the imaging element mounting section 501 outputs the obtained image signal to the signal processing section 503 via the flexible portion. The signal processing section 503 performs signal processing on the image signal output from the imaging element mounting section 501. For example, the signal processing section 503 processes the image signal, a control signal, and the like output from the imaging element mounting section 501. There is no particular limitation on the number of pixels and the resolution of the imaging element mounted on the imaging element mounting section 501; the number of pixels may be 1280×720, 1920×1080, 3840×2160, 7680×4320, or more, and the resolution may be high-definition television, 4K, 8K, or higher. An increase in the number of pixels and an increase in resolution cause an increase in heat generated from the imaging element and the signal processing section 503; hence, an embodiment of the present disclosure is more effective for an imaging element with a larger number of pixels and higher resolution.

The signal processing section 503 is electrically connected to the cable 50 via the connector connection board 600 and the hermetic connector 207. The signal processing section 503 outputs the image signal that has undergone signal processing to the cable 50 via the connector connection board 600 and the hermetic connector 207. The electronic component mounting section 505 mainly performs power supply to the signal processing section 503, power control, and the like.

The signal processing section 503 performs signal processing on the image signal, thereby generating heat. The signal processing section 503 is an example of a heat-generating section according to an embodiment of the present disclosure. Note that the technical scope of the present disclosure is not limited to the example in which the heat-generating section is the signal processing section 503, and for example, the heat-generating section may include the imaging element mounting section 501 or the like.

The connector connection board 600 couples the signal processing section 503 to the hermetic connector 207. The connector connection board 600 includes two rigid portions and a flexible portion coupling the two rigid portions. One rigid portion is connected to the rear end of the signal processing section 503, and the other rigid portion is connected to the front end portion of the hermetic connector 207. Note that details of the connector connection board 600 will be described later.

The heat transfer member 700 is a member having thermal conductivity. In an embodiment of the present disclosure, the heat transfer member 700 is interposed between the rear end of the signal processing section 503 and the front end portion of the hermetic connector 207. Thus, heat generated by the signal processing section 503 can be transferred to the cable 50 via the heat transfer member 700 and the hermetic connector 207. This increases the amount of heat transferred to the cable 50, as compared with the case where the heat transfer member 700 is not provided between the rear end of the signal processing section 503 and the front end portion of the hermetic connector 207. Consequently, heat dissipation efficiency to the outside of the camera head 40 can be improved without an increase in the size of the camera head 40. This suppresses an increase in the temperature of the imaging element inside the casing of the camera head 40 in the case of acquiring high-definition images of the observation target. Note that details of the heat transfer member 700 will be described later.

The switch connection board 800 couples the imaging element mounting section 501 to the switch 205. This allows the imaging element mounting section 501 to perform operation corresponding to a push state of the switch 205. The switch connection board 800 may be, for example, a flexible board.

2-2. Connection of Heat Transfer Member to Signal Processing Section and Hermetic Connector Next, details of connection of the heat transfer member 700 to the signal processing section 503 and the hermetic connector 207 will be described referring to FIGS. 3 and 4.

Connection Between Signal Processing Section and Hermetic Connector

Figure 3:
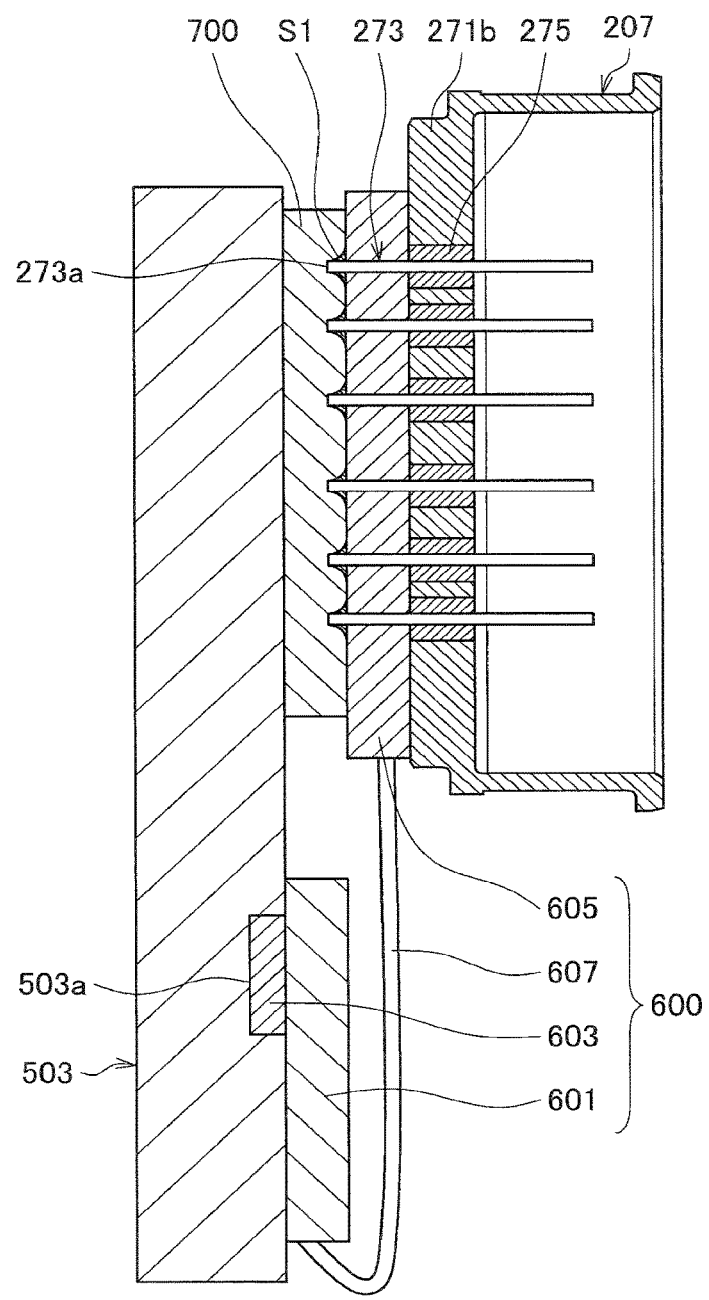
FIG. 3 is an enlarged view of a hermetic connector, a signal processing section, a connector connection board, and a heat transfer member, which are provided in the camera head according to an embodiment of the present disclosure illustrated in FIG. 2.

FIG. 3 is an enlarged view of the hermetic connector 207, the signal processing section 503, the connector connection board 600, and the heat transfer member 700, which are provided in the camera head 40 according to an embodiment of the present disclosure illustrated in FIG. 2. As illustrated in FIG. 3, the signal processing section 503 is connected to the hermetic connector 207 via the connector connection board 600. The connector connection board 600 includes a first rigid portion 601 one surface of which is provided with a terminal section 603, a second rigid portion 605, and a flexible portion 607 that couples the first rigid portion 601 to the second rigid portion 605. Connecting the signal processing section 503 to the hermetic connector 207 by the connector connection board 600 enables an image signal to be output from the signal processing section 503 to the cable 50 via the connector connection board 600 and the hermetic connector 207.

More specifically, firstly, the signal processing section 503 is provided with a terminal receptacle 503a for connecting the terminal section 603 of the connector connection board 600, like an inter-board connector that connects boards, below a portion of a rear end surface of the signal processing section 503 that is connected to the heat transfer member 700 on the paper of FIG. 3. To the terminal receptacle 503a is connected the terminal section 603 provided on the first rigid portion 601 of the connector connection board 600. Thus, the signal processing section 503 is electrically connected to the first rigid portion 601 of the connector connection board 600, which enables the signal processing section 503 to output the image signal that has undergone signal processing to the first rigid portion 601 of the connector connection board 600 via the terminal section 603.

The image signal output to the first rigid portion 601 is input to the second rigid portion 605 via the flexible portion 607. The second rigid portion 605 is provided on an end surface portion 271b of the hermetic connector 207 and electrically connected to the cable 50 via conductive pins 273 protruding from the end surface portion 271b. Note that in the present embodiment, the signal processing section 503 and the connector connection board 600 are detachably connected to each other by the terminal receptacle 503a and the terminal section 603; however, without being limited to this example, the signal processing section 503 and the connector connection board 600 may be integrally configured via the flexible portion 607, for example.

Figure 4:
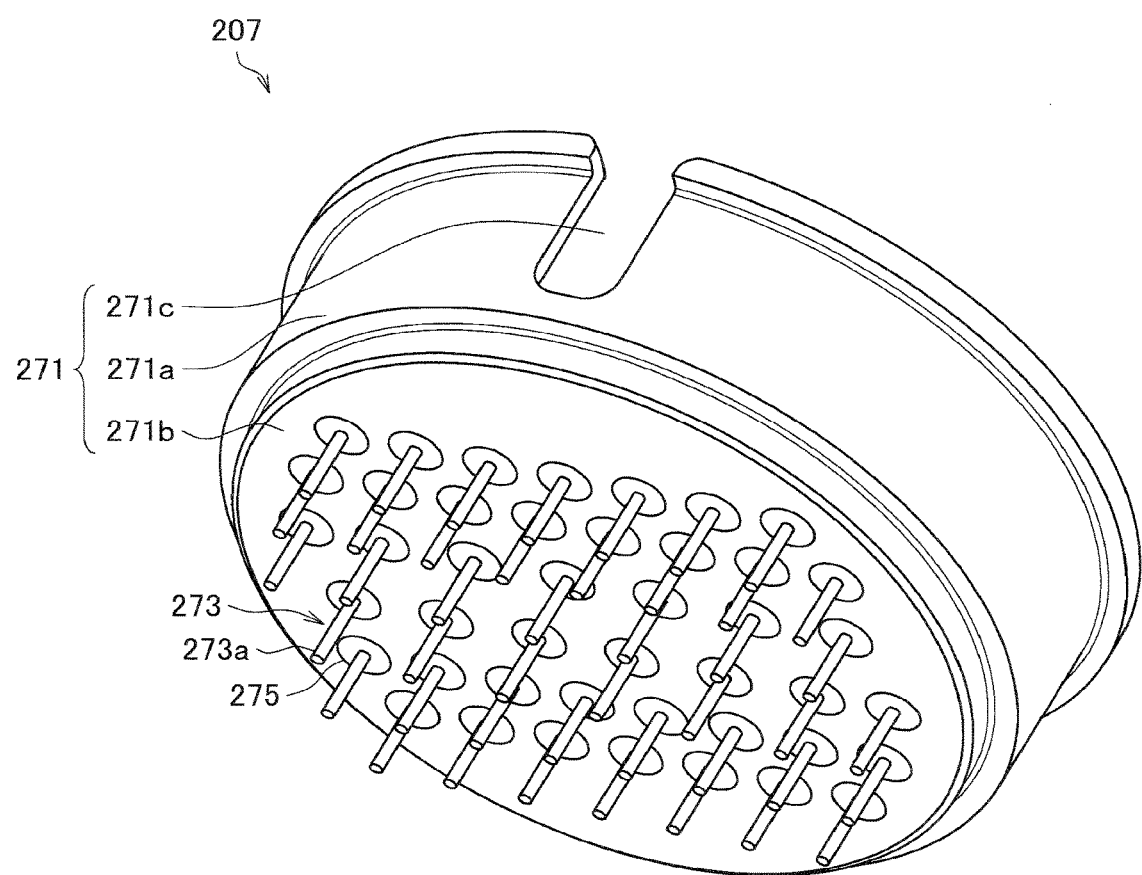
FIG. 4 is a perspective view of an example of a hermetic connector according to an embodiment of the present disclosure.

Here, a configuration of the hermetic connector 207 will be described referring to FIG. 4. FIG. 4 is a perspective view of an example of the hermetic connector 207 according to an embodiment of the present disclosure. As described using FIG. 2, the hermetic connector 207 is a connector provided so as to penetrate the rear end of the rear casing 203, and includes an outer wall 271 and the plurality of conductive pins 273.

The outer wall 271 is a metal member including a side surface portion 271a having a substantially cylindrical shape and the end surface portion 271b having a substantially circular plate shape. One end side of the side surface portion 271a having a substantially cylindrical shape is provided with the end surface portion 271b. The other end side of the side surface portion 271a is open, and the front end of the cable 50 illustrated in FIG. 2 that is connected to the hermetic connector 207 is inserted through this opening.

The end surface portion 271b is connected to the second rigid portion 605 and provided with the plurality of conductive pins 273. The conductive pins 273 are electrically conductive members each having a substantially columnar shape, and are provided so as to penetrate the end surface portion 271b, being insulated from each other by insulators 275 made of glass or the like that intervene between the conductive pins 273 and the end surface portion 271b. Front ends 273a of the conductive pins 273 protruding from the end surface portion 271b to the side opposite to the side surface portion 271a correspond to the front end portion of the hermetic connector 207 that is connected to the second rigid portion 605 of the connector connection board 600. The rear ends of the conductive pins 273 protruding from the end surface portion 271b to the side surface portion 271a side are electrically connected to the cable 50. This enables the image signal output from the second rigid portion 605 to be output to the cable 50 via the conductive pins 273. Note that in fitting the hermetic connector 207 to the rear end of the rear casing 203 illustrated in FIG. 2, an outer circumferential portion of the end surface portion 271b is joined to an inner circumferential portion of an opening of the rear end of the rear casing 203 by welding.

A notch 271c is formed by cutting off the side surface portion 271a from the opening side. To the notch 271c is fitted a projection (not illustrated) that is provided on an outer circumferential surface of the front end of the cable 50 illustrated in FIG. 2, to position and fix the cable 50 to the hermetic connector 207. There may be formed a plurality of notches 271c.

Returning to the description of FIG. 3, the second rigid portion 605 connected to such a hermetic connector 207 is provided with a plurality of through holes corresponding to the conductive pins 273 of the hermetic connector 207. The conductive pins 273 are inserted into the through holes of the second rigid portion 605, the second rigid portion 605 and the end surface portion 271b are overlapped with each other, and then the conductive pins 273 are joined to the second rigid portion 605 by soldering. FIG. 3 illustrates solder fillets S1 that are formed by soldering the conductive pins 273 to the second rigid portion 605. Thus, the image signal output from the first rigid portion 601 can be output to the cable 50 via the flexible portion 607, the second rigid portion 605, and the conductive pins 273.

Heat Transfer by Heat Transfer Member

In the camera head 40 according to an embodiment of the present disclosure, as illustrated in FIG. 3, the heat transfer member 700 is interposed between the signal processing section 503 and the front end portion of the hermetic connector 207. This allows heat to be transferred from the signal processing section 503 to the cable 50 via the heat transfer member 700 and the hermetic connector 207.

More specifically, a region of the rear end surface of the signal processing section 503 that is above a portion connected to the first rigid portion 601 is in contact with a front end surface of the heat transfer member 700. This allows heat generated by the signal processing section 503 to be transferred to the heat transfer member 700 via a contact surface between the signal processing section 503 and the heat transfer member 700. A heat-generating member may be placed on the rear end surface of the signal processing section 503, and the heat-generating member and the front end surface of the heat transfer member 700 may make surface contact. Thus, a contact area between the heat-generating member of the signal processing section 503 and the heat transfer member 700 can be increased, which increases the amount of heat transferred from the signal processing section 503 to the heat transfer member 700. Hence, the contact area between the heat-generating member of the signal processing section 503 and the heat transfer member 700 is preferably as large as possible. The thermal conductivity of the heat transfer member 700 is preferably 1 W/mK or more, further preferably 3 W/mK or more.

The heat transfer member 700 is interposed between the signal processing section 503 and the front end portion of the hermetic connector 207. Specifically, the heat transfer member 700 is interposed between an upper region of the rear end surface of the signal processing section 503 and the second rigid portion 605 provided on the end surface portion 271*b* of the hermetic connector 207. Here, as illustrated in FIG. 3, the front ends 273*a* of the conductive pins 273 of the hermetic connector 207 penetrate the second rigid portion 605 overlapped with the end surface portion 271*b* to protrude from the second rigid portion 605. Hence, by making the front ends 273*a* of the conductive pins 273 enter the heat transfer member 700 when the heat transfer member 700 is interposed between the second rigid portion 605 and the signal processing section 503, a contact area between the front ends 273*a* of the conductive pins 273 and the heat transfer member 700 can be increased. This increases the amount of heat transferred from the heat transfer member 700 to the conductive pins 273. Note that the conductive pins 273 that contact the heat transfer member 700 may be some or all of the plurality of conductive pins 273 provided for the hermetic connector 207.

The heat transfer member 700 transfers the heat transferred from the signal processing section 503 to the cable 50 illustrated in FIG. 2 via the plurality of conductive pins 273. The heat transferred to the cable 50 is dissipated to the outside via an outer sheath of the cable 50. Here, the signal processing section 503 is fixed to the rear casing 203 illustrated in FIG. 2 with a screw, for example. This allows the heat transfer member 700 to be sandwiched by the signal processing section 503, and the front ends 273*a* of the plurality of conductive pins 273 and the second rigid portion 605.

As the heat transfer member 700, a plate-shaped member having thermal conductivity, such as a silicone resin or natural rubber, may be used. It is also possible to use a gel whose main raw material is silicone, which is on the market as αGEL. The heat transfer member 700 is selected according to a balance between a heat transfer property, heat-resistant temperature, elasticity, and the like described below. The heat transfer member 700 may have heat resistance, in which case it is possible to suppress changes in the shape and physical properties of the heat transfer member 700 due to heat transferred to the heat transfer member 700. This suppresses a reduction in contact area between the heat transfer member 700 and the signal processing section 503 or the front end portion of the hermetic connector 207 and a decrease in the thermal conductivity of the heat transfer member 700. Consequently, it is possible to suppress a reduction in the amount of heat transferred from the signal processing section 503 to the cable 50. The heat-resistant temperature is preferably 140° C. or more, because temperatures up to approximately 140° C. are applied when the camera head 40 is subjected to sterilization treatment using an autoclave.

The heat transfer member 700 may have an insulating property, in which case it is possible to suppress flow of electricity in a region other than an electrical circuit that is formed by the connection of the signal processing section 503 to the hermetic connector 207 via the connector connection board 600. This suppresses unexpected malfunction and failure of components.

The heat transfer member 700 may have elasticity, in which case the heat transfer member 700 is easily deformed, which facilitates the heat transfer member 700 coming into intimate contact with members sandwiching the heat transfer member 700. This increases a contact area between the heat transfer member 700, and the signal processing section 503 and the front ends 273*a* of the plurality of conductive pins 273. Consequently, it is possible to increase the amount of heat transferred to the cable 50. The elasticity of the heat transfer member 700 is, in Asker C hardness, preferably smaller than 50, further preferably smaller than 20, still further preferably smaller than 10.

3. Effects

According to the above-described embodiment, the camera head 40 includes the heat transfer member 700 interposed between the signal processing section 503 and the front end portion of the hermetic connector 207.

Thus, heat generated by the signal processing section 503 can be transferred to the cable 50 via the heat transfer member 700 and the hermetic connector 207. This increases the amount of heat transferred to the cable 50, as compared with the case where the heat transfer member 700 is not provided between the signal processing section 503 and the front end portion of the hermetic connector 207. Consequently, heat dissipation efficiency to the outside of the camera head 40 can be improved without an increase in the size of the camera head 40. This suppresses an increase in the temperature of the imaging element inside the casing of the camera head 40 in the case of acquiring high-definition images of the observation target. Thus, high-quality images can be acquired with small size and weight.

In addition, as compared with the case where heat generated by the signal processing section 503 is dissipated to the outside by using a component such as a heat-dissipating fin, the camera head 40 can be further reduced in weight and provided at lower cost.

In addition, according to an embodiment, the first casing section 200 is at least partly grasped. When a user grasps at least part of the first casing section 200, heat dissipation efficiency from the first casing section 200 to the outside air can decrease. Even in such a case, heat generated by the signal processing section 503 can be transferred to the cable 50 via the heat transfer member 700 and the hermetic connector 207. This suppresses an increase in the temperature of the imaging element inside the casing of the camera head 40 in the case of acquiring high-definition images of the observation target.

In addition, according to an embodiment, the heat transfer member 700 makes surface contact with the heat-generating section of the signal processing section 503. Thus, a contact area between the heat transfer member 700 and the heat-generating section of the signal processing section 503 can be increased, which increases the amount of heat transferred to the cable 50.

In addition, according to an embodiment, on the signal processing section 503 is mounted a signal processing circuit including a signal processing processor that performs signal processing on the input image signal. Mounting the signal processing circuit makes the signal processing section 503 a member that generates heat easily. By interposing the heat transfer member 700 between this signal processing section 503 and the front end portion of the hermetic connector 207, it is possible to increase the amount of heat transferred from the signal processing section 503 to the cable 50. This suppresses an increase in the temperature of the imaging element inside the casing of the camera head 40 due to heat that is generated by performing signal processing on the image signal.

In addition, according to an embodiment, the cable 50 includes the second casing section 300 in contact with the first casing section 200. The second casing section 300 is made of a resin containing an electrically conductive filler. An electrically conductive filler generally has thermal conductivity. Thus, when heat distribution in the second casing section 300 becomes ununiform (e.g., when the second casing section 300 is heated locally), the heat distribution can be made uniform rapidly. This suppresses a local temperature rise in the second casing section 300 due to heat generated by the signal processing section 503.

In addition, the electrically conductive filler has electrical conductivity. This makes it possible to block electromagnetic radiation from the outside, improve the resistance of an electronic component inside the camera apparatus to static electricity, and suppress electrification of an outer surface of the camera apparatus.

In addition, according to an embodiment, the first casing section 200 includes a metal portion in contact with the second casing section 300 and the hermetic connector 207. Specifically, the metal portion is constituted by the front casing 201 and the rear casing 203. Thus, heat generated by the signal processing section 503 can be transferred to the second casing section 300, which is part of the cable 50, via the hermetic connector 207 and the metal portion. Consequently, heat dissipation efficiency to the outside of the camera head 40 can be improved without an increase in the size of the camera head 40.

In addition, according to an embodiment, the electrically conductive filler included in the second casing section 300 contains a carbon allotrope. The carbon allotrope has excellent thermal conductivity. This makes it possible to improve the thermal conductivity of the second casing section 300. In addition, the carbon allotrope is easily mixed into a resin. This makes it possible to homogenize the material constituting the second casing section 300. Thus, the distribution of physical properties, such as thermal conductivity, in the second casing section 300 can be made substantially uniform.

4. Conclusion

As described above, according to an embodiment of the present disclosure, there is provided a medical camera head including a first casing configured to accommodate an imaging element, a heat-generating section accommodated in the first casing, a connection section provided in the first casing, an external signal transmission section being connected to one end of the connection section, and a heat transfer member interposed between the heat-generating section and the other end of the connection section.

Thus, heat generated by the heat-generating section can be transferred to the signal transmission section via the heat transfer member and the connection section. This increases the amount of heat transferred to the signal transmission section, as compared with the case where the heat transfer member is not interposed between the heat-generating section and the front end of the connection section. Consequently, heat dissipation efficiency to the outside of the camera head can be improved without an increase in the size of the camera head. This suppresses an increase in the temperature of the imaging element inside the first casing of the camera head in the case of acquiring high-definition images of the observation target. Thus, high-quality images can be acquired with small size and weight.

In addition, as compared with the case where heat generated by the heat-generating section is dissipated to the outside by using a component such as a heat-dissipating fin, the camera head can be further reduced in weight and provided at lower cost.

Described above is the camera head including the hermetic connector 207, which is a connector section provided in the first casing, an external cable being detachably connected to one end of the connector section. It is also possible, however, to employ a configuration in which, for example, an external cable not having a connector section is integrally connected by directly connecting signal lines of the external cable to the conductive pins 273 joined to the second rigid portion 605 illustrated in FIG. 3.

Described above is an example in which the camera head according to an embodiment of the present disclosure is used for an endoscope apparatus, but a medical camera apparatus including the camera head according to an embodiment of the present disclosure is not limited to this example. For example, the medical camera apparatus according to an embodiment of the present disclosure may be a medical microscope apparatus. The medical microscope apparatus is a camera apparatus used for carrying out surgical operations while observing a portion to be operated on under magnification. The medical microscope apparatus includes an imaging apparatus and an arm apparatus capable of holding the imaging apparatus and moving and fixing a position and an attitude of the imaging apparatus. The camera head according to an embodiment of the present disclosure can be, for example, used as the imaging apparatus of such a medical microscope apparatus. In addition, the signal transmission section according to an embodiment of the present disclosure can be, for example, used as the arm apparatus of such a medical microscope apparatus. In such a medical microscope apparatus, the arm apparatus may hold two camera heads.

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1) A medical camera head including:
a first casing configured to accommodate an imaging element;
a heat-generating section accommodated in the first casing;
a connection section provided in the first casing, an external signal transmission section being connected to one end of the connection section; and
a heat transfer member interposed between the heat-generating section and the other end of the connection section.

(2) The medical camera head according to (1),
wherein the connection section is a connector section to which the external signal transmission section is detachably connected.

(3) The medical camera head according to (1) or (2),
wherein the first casing is at least partly grasped.

(4) The medical camera head according to any one of (1) to (3),
wherein the heat transfer member makes surface contact with a heat-generating member of the heat-generating section.

(5) The medical camera head according to any one of (1) to (4),
wherein a signal processing circuit configured to perform signal processing on an input image signal is mounted on the heat-generating section.

(6) A medical camera apparatus including:
the medical camera head according to any one of (1) to (5); and
the signal transmission section connected to the connection section of the medical camera head.

(7) The medical camera apparatus according to (6),
wherein the signal transmission section includes a second casing in contact with the first casing, and
wherein the second casing is made of a resin containing an electrically conductive filler.

(8) The medical camera apparatus according to (7),
wherein the first casing includes a metal portion in contact with the second casing and the connection section.

(9) The medical camera apparatus according to (7) or (8),
wherein the electrically conductive filler contains a carbon allotrope.

(10) A medical camera apparatus including:
a medical camera head including
a first casing that is configured to accommodate an imaging element and at least partly includes a metal portion,
a heat-generating section accommodated in the first casing, and
a heat transfer member interposed between the heat-generating section and the metal portion; and
a signal transmission section that includes a second casing and is connected to the medical camera head, the second casing being in contact with the metal portion of the first casing and made of a resin containing an electrically conductive filler.

(11) The medical camera apparatus according to (10),
wherein the metal portion includes a connection section to which the signal transmission section is connected, and
wherein the connection section is a connector section to which the external signal transmission section is detachably connected.

(12) The medical camera apparatus according to (10) or (11),
wherein the first casing is at least partly grasped.

(13) The medical camera apparatus according to any one of (10) to (12),
wherein the heat transfer member makes surface contact with a heat-generating member of the heat-generating section.

(14) The medical camera apparatus according to any one of (10) to (13),
wherein a signal processing circuit configured to perform signal processing on an input image signal is mounted on the heat-generating section.

(15) The medical camera apparatus according to any one of (10) to (14),
wherein the electrically conductive filler contains a carbon allotrope.

What is claimed is:

1. A medical camera head comprising:
a first casing configured to accommodate an imaging element;
a heat-generating section accommodated in the first casing;
a connection section provided in the first casing, wherein an external signal transmission section is connected to one end of the connection section; and
a heat transfer member having elasticity and being sandwiched between the heat-generating section and the other end of the connection section,
wherein a signal processing circuit configured to perform signal processing on an input image signal is mounted on the heat-generating section, and
wherein the connection section electrically connects the signal processing circuit to outside of the medical camera head via the external signal transmission section via pins.

2. The medical camera head according to claim 1,
wherein the connection section is a connector section to which the external signal transmission section is detachably connected.

3. The medical camera head according to claim 1,
wherein the first casing is at least partly grasped.

4. The medical camera head according to claim 1,
wherein the heat transfer member has a plate shape, and one surface of the heat transfer member is in contact with a surface of the heat-generating section and the other surface of the heat transfer member is in contact with a surface of the other end of the connection section.

5. A medical camera apparatus comprising:
the medical camera head according to claim 1; and
the signal transmission section is connected to the connection section of the medical camera head.

6. The medical camera apparatus according to claim 5,
wherein the signal transmission section includes a second casing in contact with the first casing, and
wherein the second casing is made of a resin containing an electrically conductive filler.

7. The medical camera apparatus according to claim 6,
wherein the first casing includes a metal portion in contact with the second casing and the connection section.

8. The medical camera apparatus according to claim 6,
wherein the electrically conductive filler contains a carbon allotrope.

* * * * *